US006653153B2

(12) United States Patent
Xiong et al.

(10) Patent No.: US 6,653,153 B2
(45) Date of Patent: Nov. 25, 2003

(54) METHODS FOR ENCODING COMBINATORIAL LIBRARIES

(75) Inventors: Yusheng Xiong, Plainsboro, NJ (US); Kevin Chapman, Scotch Plains, NJ (US); Tiebang Wang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 5 days.

(21) Appl. No.: 09/898,142

(22) Filed: Jul. 3, 2001

(65) Prior Publication Data

US 2002/0022237 A1 Feb. 21, 2002

Related U.S. Application Data

(60) Provisional application No. 60/215,834, filed on Jul. 3, 2000.

(51) Int. Cl.[7] ...................... G01N 33/545; C07D 29/44; C07K 1/04
(52) U.S. Cl. ........................... 436/531; 435/4; 436/518; 436/545; 436/120; 546/207; 546/208
(58) Field of Search ............................ 435/4, 174, 180; 436/518, 84, 85, 100, 102, 120, 528, 531; 546/207, 208

(56) References Cited

U.S. PATENT DOCUMENTS 5,494,649 A * 2/1996 Fristad et al. .................. 423/27

FOREIGN PATENT DOCUMENTS

WO  WO 96/30392  * 10/1996  ............ C07K/1/04

* cited by examiner

*Primary Examiner*—Padmashri Ponnaluri
*Assistant Examiner*—My Chau T. Tran
(74) *Attorney, Agent, or Firm*—James L. McGinnis; Melvin Winokur

(57) ABSTRACT

A combinatorial library comprises a plurality of ligand-bearing support units, where the ligand-bearing support units comprise (a) a solid carrier, (b) one or more ligands covalently bound to the solid carrier, and (c) one or more encoding metal salts impregnated on the support unit, where the distribution of the cations of the encoding metal salts provides a code for identifying the ligand or ligands that are attached to the support units, and the cations have been stabilized against dissolution by treatment with one or more anions that form insoluble or poorly soluble salts of the cations.

20 Claims, No Drawings

METHODS FOR ENCODING COMBINATORIAL LIBRARIES

CROSS REFERENCE TO RELATED APPLICATIONS

This application is based on and claims priority from U.S. Provisional Application No. 60/215,834, which was filed on Jul. 3, 2000, and which is incorporated by reference into this application.

FIELD OF THE INVENTION

This invention relates to combinatorial chemistry, and more specifically to combinatorial libraries comprising solid supports in the form of support units (particles, beads and the like), each of which is labeled with one or more metals that provide a code for identifying the compounds that are or were attached to the bead.

BACKGROUND OF THE INVENTION

In the field of combinatorial chemistry, libraries of chemical compounds are made for screening to determine which chemical compounds are active for a particular use, such as agonism or antagonism of a receptor. Usually this screening is carried out by performing assays on each member of the library or groups of members of the library. The compounds that have the desired activity as determined by the assay method are then made on a larger scale for more thorough testing.

Numerous strategies have been designed for testing and tracking the compounds being tested in these mass screenings so that the compounds that have activity in the assays can be readily identified after a positive assay. One of these strategies involves the synthesis of compounds (often referred to as ligands) on the solid support units such that each support unit carries a single compound. The compounds can then be assayed individually, either while they are still attached to the support unit, or more typically, after being cleaved from the support unit. Identification of the compound that is or was on the support unit after a positive assay result is still an ongoing source of difficulty. Since large numbers of support units are used (typically in the hundreds or thousands), the individual support units are not handled and tracked separately. For example, in a split pool synthesis, the support units are synthesized and manipulated in groups for each synthetic step and for assays. Even though each support unit may have only one kind of ligand bound to it, the individual support units are mixed with a large number of other support units, each having a different ligand bound to it. This kind of mass screening makes it impractical or impossible to keep track of the individual ligands as they are synthesized and assayed. As a result, after the assays have been completed, the ligands that are present on the beads that have the desired activity must still be identified. Either the ligand can be analyzed, as by mass spectrometry, or the ligand can be identified based on information contained in the support unit to which it is or was previously attached. To make analysis of the compound (the ligand) being assayed easier, schemes have been developed for encoding the support units by placing chemical markers or "tags" on the support units and then using those tags to identify the chemical compound (ligand) that was originally synthesized on the support unit.

These chemical markers have taken at least two forms. In one, a unique sequencable oligomer, such as a polynucleotide or polypeptide oligomer, is synthesized in parallel with the compound that is being tested on the support unit. The nucleotide or peptide sequence is then determined for the units that have positive assays to determine the compound that has the desired activity in the assay. See for example, WO 93/06121; Brenner, et al., Proc. Natl. Acad. Sci. USA (1992), 89, 5381; Kerr, et al., J. Am. Chem. Soc (1993), 115, 2529; Lebl, Pept. Res. (1993), 6 (3), 161; and Lebl, Proc Natl. Acad. Sci. USA, (1996), 93, 8194. This approach to chemical coding requires the synthesis of a complete second, parallel library of oligomers that serve as chemical markers. This method can be very cumbersome and has the limitation that the syntheses of the oligomer/chemical marker and the molecules being tested must be compatible with one another.

A second approach to marking the support units involves attaching combinations of chemical markers to the support unit. In this approach, the information that identifies the support unit is carried in the combination of what markers are present and what markers are not present, and does not rely on the sequence of the markers. The chemical markers can each be attached directly to the support unit in some way or can be attached to each other and then attached as a group to the support unit. The information needed to identify the chemical compound that was synthesized on the support unit for testing is not retrieved by sequencing the markers, but rather is obtained by determining which markers are present and which markers are absent. This approach is inherently easier, since making and then later analyzing a molecular sequence is much more time consuming and difficult than just creating a code by attaching individual markers to a support and then later determining what markers are present without having to determine the order in which they are attached. Furthermore, only a few kinds of sequences can be determined using automated technology, such as polypeptides and polynucleotides.

The chemical markers can be used to provide a code, based on which chemical markers are present and which markers are absent. One very convenient and efficient kind of code is a binary code, where each chemical marker is represented as a digit in a binary number, with its presence or absence representing the two choices (i.e. "1" or "0") for the binary digit. Examples of organic chemical markers that have been used in this approach include aryl ether carbenes, which are attached to the support unit at low levels compared with the molecule being synthesized during each step of a split pool synthesis, and are then decoded by cleavage of the aryl carbene residues from the support unit followed by gas chromatographic analysis. See for example, Still, et al. U.S. Pat. No. 5,563,324; Still et al., WO 94/08051; Still et al., WO 95/26640; Still et al., Proc. Natl. Acad. Sci. USA (1993), 90, 10922. Another example of a binary encoding scheme using organic markers is based on secondary amines assembled as N-amidomethyl polyglycines, Ni, et al, J. Med. Chem. (1996), 1601; Gallop, et al., U.S. Pat. No. 5,846,839.

Other methods for encoding support units use physical encoding, such as bar codes, as for example WO 97/15390. Radio frequency has also been utilized, as for example by IRORI, in Ang. Chem. Int. Ed. Engl. (1995), 34 (20), 2289; Ontogene, in J. Am. Chem. Soc. (1995), 117, 10787; and Mandecki, in WO 97/19958. Other marking methods include fluoroescence encoding, as for example in WO 95/32425 and Egner et al., Chem. Comm (1997), 735; and isotope ratio encoding, as for example in Geysen, et al., Chem. Biology (1997), 3 (8), 679; Geysen et al., WO 97/37953; Wagner et al, Combinatorial Chem. High Throughput Screening (1998), 1, 143; and Weinstock et al., WO 97/29371. These methods all have limited utility for general combinatorial libraries.

A variation on chemical encoding involves the use of metal ions rather than organic chemical residues to encode combinatorial libraries on solid supports. See Rink, et al., WO 96/30392, which reference is incorporated by reference into this application in its entirety. In this method, soluble salts (e.g. nitrates) of the lanthanide metal series are absorbed into the support units at each step of the split pool synthesis of the organic compounds (ligands) that are being attached to the support units. The metal salts in solution are added to the beads, which are suspended in the solvent.

A different metal salt or salts may be added to the support after each new step in the split pool synthesis. Analysis of the metal content of the support units and comparison with a key of what the various metals represent enables identification of the compounds.

Although the metal salts are not covalently attached to the support units, they are reported to remain in the beads throughout the synthesis in the form of soluble salts. The inventors report that sufficient quantities of the soluble metal salts "surprisingly" remain in the beads through the subsequent reaction steps so that the presence or absence of the metal salts can be determined at the end of the process by methods that are customarily used in the analysis of elements or element ions, such as total reflection x-ray fluorescence spectrometry (TRXF), neutron activation followed by gamma spectrometry, or mass spectrometry, particularly inductively coupled plasma-mass spectrometry (ICP-MS).

However, the use of soluble metal salts can result in the loss of metal ions and/or crossover of metal ions between support units, making analysis difficult and/or uncertain. This can happen even under ideal conditions, and is more likely to happen if conditions are not ideal, as for example, if the solvent is heated, if the solvent contains or can act as a ligand for the metal ion, or if the metal salt is highly soluble in the solvent. Leaching and loss of the salts and crossover to other beads was observed with the salts that were used in the experiments disclosed herein. There is therefore a need to have support units and methods of preparing support units that are labeled with metal ions or other markers and that are stable to varied conditions, such as temperature, organic reagents, and solvents.

SUMMARY OF THE INVENTION

In the present invention, a solution of a soluble salt, the anion of which forms insoluble salts with the metal cations that are used to label ("encode") the support units, is added to the labeled support units to prevent or decrease the loss of the metal used to label the support units. Loss of metal is believed to be prevented by the formation of insoluble or poorly soluble salts of the metals that are used to label the support units. Support units are the individual units of solid support that are used. Support units are generally beads, preferably porous beads.

For example, the support units can first be labeled with one or more metal salts in solution (e.g. $AgNO_3$ in water). The metal-labeled support units can then be treated with a solution of $Na_2S$, which is expected to form an insoluble salt of the metal that is used as a label (e.g. $Ag_2S$). When this method is used, support units that are labeled with metal tags (salts) do not lose their metal labels as readily, if at all. The labeled support units are more stable to the harsh reaction conditions that are often needed for the synthesis or cleavage of the ligands, such as for example heating the support to 70° C. in acetic acid overnight, without loss of the metal tags.

Another means of achieving improved retention of metal is to include linker groups that contain as part of their structure a moiety, such as sulfur, that forms non-covalent bonds to the labeling metals. A linker is one molecule or two or more molecules covalently bound together, where the linker connects the ligand to the functional groups of the support unit. Linkers generally have two reactive functional groups so that they can be connected to the support unit and to the ligand. Commonly used linkers include 4-hydroxymethylbenzoic acid (HMBA) and 4-hydroxymethylphenylacetic acid. These linkers are used because they are stable to cleavage under reaction conditions typically encountered in preparing a combinatorial library, but at the same time they are readily cleaved under a particular set of reaction conditions. A standard kind of linker molecule, such as HMBA, can be bound to a sulfur-containing molecule or molecules to form a linker that also includes a sulfur-containing moiety to achieve good bonding to the metals and also to achieve the properties typically desired from linkers.

When sulfur or another moiety that forms non-covalent bonds to the labeling metals is present in the linker molecules or elsewhere in the support units, the uptake and retention of the encoding metal salts by the resin is improved. For example, the carboxyl end of a tripeptide of methylated cystein can be attached to the amine groups of aminomethyl polystyrene to form a "pre-sulfurized resin," where the pre-sulfurized resin is in the form of a bead. A hydroxymethylbenzoic acid (HMBA) molecule can then be attached to the free amine group of the tripeptide, and the sub-units of the ligand can be attached one sub-unit at a time in sequence to the hydroxy end of the HMBA to form the ligand on the support unit.

Use of beads or support units comprised of the pre-sulfurized resin encoded with metal cations gives better retention of the metal ion, minimizes cross contamination of the labeling metals between the support units, and results in a faster and more accurate determination of the code that is on the bead or support unit.

Furthermore, the combination of both of the above methods of stabilizing the metal on the support unit, i.e. by: (1) attaching sulfur-containing linker molecules to the support unit, and (2) treating the metal-labeled support units with a solution of an anion that forms poorly soluble or insoluble salts of the labeling metals, gives even better, more reliable retention of the labeling metals, and so far is the best way of using metal cations to encode the ligands of a combinatorial library.

This approach to encoding the support has the advantage of causing only minimal restrictions in the kinds of chemical reagents, solvents and conditions that can be used in the library synthesis, and also allows fast decoding without the necessity of cleaving the metal tags off of the solid support. Decoding of the metal is most conveniently done by mass spectral analysis, such as inductively coupled plasma mass spectrometry (ICP-MS). The preferred mass spectral process for decoding is a laser ablation-ICP-MS technique. This method requires very little time (less than 20 seconds) to decode each bead. The laser ablation equipment can be automated to scan large numbers of beads in arrays on plates. This method therefore offers the capability of decoding a whole library automatically, making it possible to obtain a detailed structure-activity relationship (SAR) from biological screening. Most other encoding-decoding methods previously used are not readily automated and are therefore only suitable for decoding a few active beads in a particular assay, with each new assay of a library sample requiring a different decoding step.

The present invention is a method of using and stabilizing metal salts to encode combinatorial support units in the preparation of combinatorial libraries. The invention is also a method of making encoded combinatorial libraries and of decoding combinatorial libraries to determine what ligands are on particular beads or have particular kinds of activity. The combinatorial support units and the libraries that are made using this methodology are all new.

DETAILED DESCRIPTION OF THE INVENTION

A combinatorial library of this invention comprises a plurality of ligand-bearing support units, where the ligand-bearing support units comprise (a) a solid carrier, (b) one or more ligands covalently bound to the solid carrier, and (c) one or more encoding metal salts impregnated on the support unit, as follows:

(a) The carrier is the material that forms the support unit and contains functional groups to which the ligands are covalently bound, where the functional groups and the ligands are optionally connected by linker groups. The linker groups are organic residues that connect the carrier and the ligand and are covalently bound both to the solid carrier and to the ligand .

(b) The ligand is an organic compound covalently bound to the functional groups of the carrier or to the linker groups.

(c) The encoding metal salts include one or more encoding metal cations, which are distributed in their natural isotope abundance or in non-natural isotope abundances, where the distribution of the encoding metal cations provides a code for identifying the ligand or ligands that are attached to the support unit, and one or more anions that form insoluble or poorly soluble salts of the encoding metal cations in the solvent or solvents which are used to prepare the combinatorial library.

The metals that are used as labels can be used in their natural isotope abundances. Alternatively, other isotope abundances, which would be man-made (non-natural), can also be used. Generally, this would be a single isotope, which makes quantitative mass spectral measurement easier. The use of single isotopes also is advantageous in that it greatly increases the number of possible labels.

"Insoluble" and "poorly soluble" conform with common usage. Salts that are insoluble or poorly soluble precipitate out of solution when solutions containing the cations and anions are mixed. The salts do not dissolve appreciably.

In the combinatorial library described above, the ligand may consist of two or more sub-units which are covalently bound to each other, and which are generally assembled sequentially on the support unit. The ligand is the organic compound whose chemical, biological, or other activity is being evaluated.

The encoding metal salts in this combinatorial library are impregnated onto the support unit by treating the support unit with a solution of a soluble salt of the encoding metal cations to form a support unit which is labelled with a soluble encoding metal salt, and then treating the support unit having the soluble encoding metal salt with a solution of a salt having an anion that forms insoluble or poorly soluble salts when combined with the encoding metal cations. This yields a stabilized encoding metal salt, wherein the salt has been stabilized against dissolution from the support unit.

In the combinatorial library described above, the solid carrier is generally a synthetic polymeric compound, and the support units are usually in the form of beads, particularly porous beads. The polymeric compound is normally polystyrene, optionally crosslinked with divinylbenzene, where the polystyrene includes functional groups that can react with other compounds. The ligands or the optional linker groups are bound to the functional groups of the polystyrene.

In preferred embodiments of the combinatorial library described above, the carrier and/or the optional linker groups includes one or more moieties that enhances the uptake and retention of the encoding metal salt. Preferably these moieties are in the linker groups. These moieties increase the initial loading of metal ions in the solid support and decrease the solubility of or rate of dissolution of the encoding metal salt by acting as a ligand that is non-covalently bound to the encoding metal cation.

In the combinatorial library, the encoding metal salts that are stabilized against dissolution include encoding metal cations which form soluble salts with one or more anions selected from the group consisting of nitrates, hydroxides, chlorides, acetates, and sulfates, and the encoding metal cations form insoluble or poorly soluble salts with one or more anionic groups selected from the group consisting of sulfides, sulfates, oxides, hydroxides, halides and carbonates. The encoding metal cations are usually selected from the group consisting of the transition metals, the lanthanides, the actinides, Sr, Ba, Tl, In, Sb, and Bi. Often, the encoding metal cations are selected from the group consisting of the Group VIIIB, IB and IIB transition metals. Preferred encoding metal cations include Pd, Ru, Rh, Pt, Ag, Ni, Cu, Co and Hg, including individual isotopes of each of these metals.

In many cases, the encoding metal salts are stabilized against dissolution by treatment with a solution of sulfide salts or precursors that can generate sulfide ions in situ.

This invention also is an improvement in combinatorial libraries that include a plurality of support units, wherein each support unit comprises (a) a solid carrier, (b) one or more ligands covalently bound to the solid carrier or to a linker group that is covalently bound to the solid carrier, and (c) one or more encoding metal salts impregnated on the support unit, where the encoding metal salts include encoding metal cations, and the distribution of the cations provides a code that identifies the ligand or ligands. The improvement is that the support unit also includes one or more anions that form insoluble or poorly soluble salts of the encoding metal cations in the solvent or solvents which are used to prepare the combinatorial library.

The combinatorial library is improved in that the encoding metal salts are impregnated onto the support unit by first treating the support unit with a solution of a soluble salt of the encoding metal cations to form a support unit labelled with a soluble encoding metal salt, and then treating the support unit including the soluble encoding metal salt with a solution of a salt that includes an anion that forms insoluble or poorly soluble salts when combined with the encoding metal cations, thereby stabilizing the encoding metal salt against dissolution from the support unit.

A further improvement is achieved when the support units include linker groups covalently bound to the solid carrier, where the linker groups include one or more moieties that enhances the uptake and retention of the encoding metal ions. An example would be a sulfur-containing linker group.

The invention furthermore is a method of preparing an encoded combinatorial library which includes a plurality of ligand-bearing support units, wherein the ligand-bearing support units include (a) a solid carrier, (b) one or more ligands covalently bound to the solid carrier, and (c) a plurality of encoding metal salts impregnated on the support unit, the metal salts providing a code for identifying the ligand. The method includes the steps of:

(1) providing support units which include a solid carrier having functional groups, the functional groups being optionally connected to linker groups, the linker groups being organic residues covalently bound to the functional groups of the solid carrier and having functional groups for covalent binding to the ligand;

(2) covalently attaching a ligand or a first sub-unit of a ligand that will have more than one sub-unit to the functional group of the carrier or to the functional group of an optional linker group, in which case the sub-unit has a functional group for covalent binding to a second sub-unit; and (3) impregnating the support unit with one or more encoding metal salts, the salts being composed of one or more encoding metal cations, which are distributed in their natural isotope abundance or in a non-natural isotope abundance, where the encoding metal cations provide a code for identifying the ligand or sub-unit that is attached to the support unit, and the encoding metal salts are impregnated onto the support unit by treating the support unit with a solution of a soluble salt of the encoding metal cations to form a support unit labeled with the soluble encoding metal salts, and then treating the support unit which contains the soluble encoding metal salts with a solution of a salt having an anion that forms insoluble or poorly soluble salts when combined with the encoding metal salts, thereby yielding a stabilized encoding metal salt, which is stabilized against dissolution from the support unit;

wherein step (3) can be carried out before or after step (2) or concurrently with step (2).

The method of preparing an encoded combinatorial library which contains a plurality of ligand-bearing support units, as recited above, wherein the ligands comprise two or more sub-units, comprises the further steps of:

(1) covalently attaching a second sub-unit to the functional group of the first sub-unit, where the second sub-unit may be the same as the first sub-unit or different, where the second sub-unit optionally has a functional group that optionally may be used for adding a third sub-unit;

(2) impregnating the support unit with one or more encoding metal salts, the salts being composed of one or more encoding metal cations, where the encoding metal cations are distributed in their natural isotope abundance or in a non-natural isotope abundance, wherein the encoding metal cations provide a code for identifying the second sub-unit, wherein the encoding metal salts are impregnated onto the support unit by treating the support unit with a solution of a soluble salt of the encoding metal cation to form a support unit labelled with a soluble encoding metal salt, and then treating the support unit labelled with the soluble encoding metal salt with a solution of a salt having an anion that forms insoluble or poorly soluble salts when combined with the encoding metal cations, thereby yielding a stabilized encoding metal salt, which is stabilized against dissolution from the support unit; and (3) optionally repeating steps (1) and (2) one or more times to add additional sub-units to form a ligand comprising a plurality of sub-units, where the ligand is identifiable by measurement of the distribution of metal cations on the support unit;

wherein step (1) can be carried out before or after step (2) or concurrently with step (2) in each repetition of steps (1) and (2).

A method of preparing an encoded combinatorial library including a plurality of ligand-bearing support units, where the ligand-bearing support units include (a) a solid carrier, (b) one or more ligands covalently bound to the solid carrier, where the ligands are comprised of two or more sub-units, and (c) a plurality of encoding metal salts impregnated on the support unit, the metal salts providing a code for identifying said ligand, comprises the steps of:

(1) providing support units comprising a solid carrier having functional groups, the functional groups being optionally connected to linker groups, the linker groups being organic residues covalently bound to the functional groups of the solid carrier and having functional groups for covalent bonding to the ligand;

(2) covalently attaching a first sub-unit to the functional group of the carrier or to the functional group of the optional linker group (which may consist of more than one molecule bound together, the sub-unit having a functional group for covalent bonding to a second sub-unit;

(3) impregnating the support unit with one or more encoding metal salts, the salts being comprised of one or more encoding metal cations, said encoding metal cations being distributed in their natural isotope abundance or in a non-natural isotope abundance, wherein the combination of encoding metal cations provides a code for identifying the sub-unit that is attached to the support unit, wherein the encoding metal salts are impregnated onto the support unit by treating the support unit with a solution of a soluble salt of the encoding metal cation to form a support unit comprising the soluble encoding metal salt, and then treating the support unit comprising the soluble encoding metal salt with a solution of a salt having an anion that forms insoluble or poorly soluble salts when combined with the encoding metal cations, thereby yielding an encoding metal salt that is stabilized against dissolution from the support unit;

(4) covalently attaching a second sub-unit to the functional group of the first sub-unit, wherein the second sub-unit may be the same as the first sub-unit or different, and the second sub-unit optionally has a functional group that optionally may be used for adding a third sub-unit;

(5) impregnating the support unit with one or more encoding metal salts, the salts being comprised of one or more encoding metal cations, which are distributed in their natural isotope abundance or in a non-natural isotope abundance, where the encoding metal cations provide a code for identifying the second sub-unit; the encoding metal salts are impregnated onto the support unit by treating the support unit with a solution of a soluble salt of the encoding metal cation to form a support unit comprising a soluble encoding metal salt, and then treating the support unit comprising the soluble encoding metal salt with a solution of a salt having an anion that forms insoluble or poorly soluble salts when combined with the encoding metal cations, thereby yielding an encoding metal salt that is stabilized against dissolution from the support unit;

(6) optionally repeating said steps (4) and (5) one or more times to add additional sub-units to form a ligand comprising a plurality of sub-units, where the ligand is identifiable by measurement of the distribution of metal cations on said support unit;

wherein step (2) can be carried out before or after step (3) or concurrently with step (3), step (4) can be carried out before or after step (5) or concurrently with step (5), and in subsequent repetitions of steps (4) and (5) as recited in step (6), step (4) can be carried out before or after step (5) or concurrently with step (5).

In the above description of the method of making the encoded support units, the encoding steps and the steps where sub-units are added are generally part of a split-pool synthesis, which means that the steps described above are carried out on groups of support units rather than individual support units. It also means that after each pair of steps where a ligand or ligand sub-unit is added, along with the addition of a label, the group of support units may be combined with other support units or groups of support units, or the group of support units may be separated into smaller groups, which groups may then be combined with other support units or groups of support units before the next step.

The invention is also an improved method of preparing a combinatorial library comprising a plurality of support units, wherein each support unit comprises (a) a solid carrier, (b) one or more ligands covalently bound to the solid carrier or to a linker group that is covalently bound to the solid carrier, and (c) one or more encoding metal salts impregnated onto the support unit, wherein said encoding metal salts include encoding metal cations, the distribution of the cations providing a code that identifies the ligand or ligands. The improvement is that the encoding metal cations are stabilized against dissolution by treatment of the support units with a solution that comprises one or more anions that form insoluble or poorly soluble salts of said encoding metal cations in the solvent or solvents which are used to prepare said combinatorial library, thereby yielding an encoding metal salt that is stabilized against dissolution.

The combinatorial libraries made by any of the methods described above are also new.

Finally, the method of analyzing the ligands present on the support units in the combinatorial libraries described above utilizes the information encoded in the metal labels. The method of determining the ligand on a single support unit includes the steps of (1) providing a support unit from the library of support units that have ligands and metal labels; (2) analyzing which metal ions are present on the support unit, and (3) comparing the metal ion content with the code information to determine what ligand was synthesized on the support unit.

The metal ion content of the support unit is analyzed using inductively coupled plasma mass spectrometry, and particularly laser ablation inductively coupled plasma mass spectrometry (laser ablation ICP-MS). Laser ablation ICP-MS is an excellent method for carrying out rapid screening of a large number of samples and can be adapted to the screening of an array of samples, such as might be found on a micro-titer plate. An example of an instrument that can be adapted to the analysis of arrays of beads on micro-titer plates is a Perkin Elmer Elan 2000 ICP-MS, coupled with an LSX-200 laser ablation unit from CETAC. Resin beads are plated onto the sample holder and are either scanned with a laser beam or drilled with a laser beam.

The following examples are provided to illustrate the invention. The invention is not to be construed as limited to these specific examples. The scope of the invention is defined by the claims.

EXAMPLES

Methods and Materials

The resin used in the examples is aminomethyl functionalized polystyrene beads purchased from LCC Engineering and Trading GMBH (HAT-106-1.1AM). The loading level is 1.1 mmole/g.

HMBA linker was attached to the resin by standard methods using 3 equivalents of 4-hydroxymethylbenzoic acid (HMBA), 4 equivalents of HOBt, 3 equivalents of DIC, and 3% of DMAP as catalyst. All reagents were combined in DMF to yield an approximately 0.4M HMBA concentration prior to mixing with the resin. The resin suspension was allowed to stand at room temperature for about 3 hours, followed by washing (DDMF 4×, THF-DCM 3×) and drying in vacuo.

The pre-sulfurized resin, when used, was derived from the LCC aminomethyl functionalized polystyrene beads by first attaching to the resin a tripeptide sequence, using methylated cystein as the peptide. The resin was suspended in a DMF solution of 3 equivalents of Fmoc-Cys(Me)-OH and 3 equivalents of DIC at 0.25 M concentration for 3 hours. After washing with DMF (3×), the resin was treated with piperidine/DMF (25%) to remove the Fmoc protection. This procedure was repeated two more times to form a tripeptide of Cys(Me)-$NH_2$ resin. HMBA was then attached to the $NH_2$ end group as before.

Example 1

This example shows that resins with different functional groups have different capabilities for absorbing and retaining metals. It also illustrates that the metal salt labeling of the resin does not affect the yield or purity of product that is made on the resin. Table 1 below shows the experimental results.

In this example, a 3-substituted-2-phenylindole is synthesized on polystyrene beads using the Fischer indole synthesis. An example is shown in the scheme below. In the scheme below, a 4-hydroxymethylbenzoic acid linker (HMBA) is attached to the amine group of polystyrene beads having an amine functionality before the Fischer indole synthesis is carried out on the resin. Table 1 below shows the results for several different experiments using metal salt labels and polystyrene beads. The scheme below shows the synthesis of a 3-substituted-2-phenylindole, but other 2-arylindoles can also be made by analogous methods. Similarly, other 2-substituents can also be made by analogous methods.

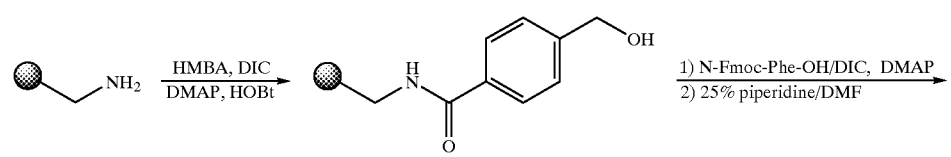

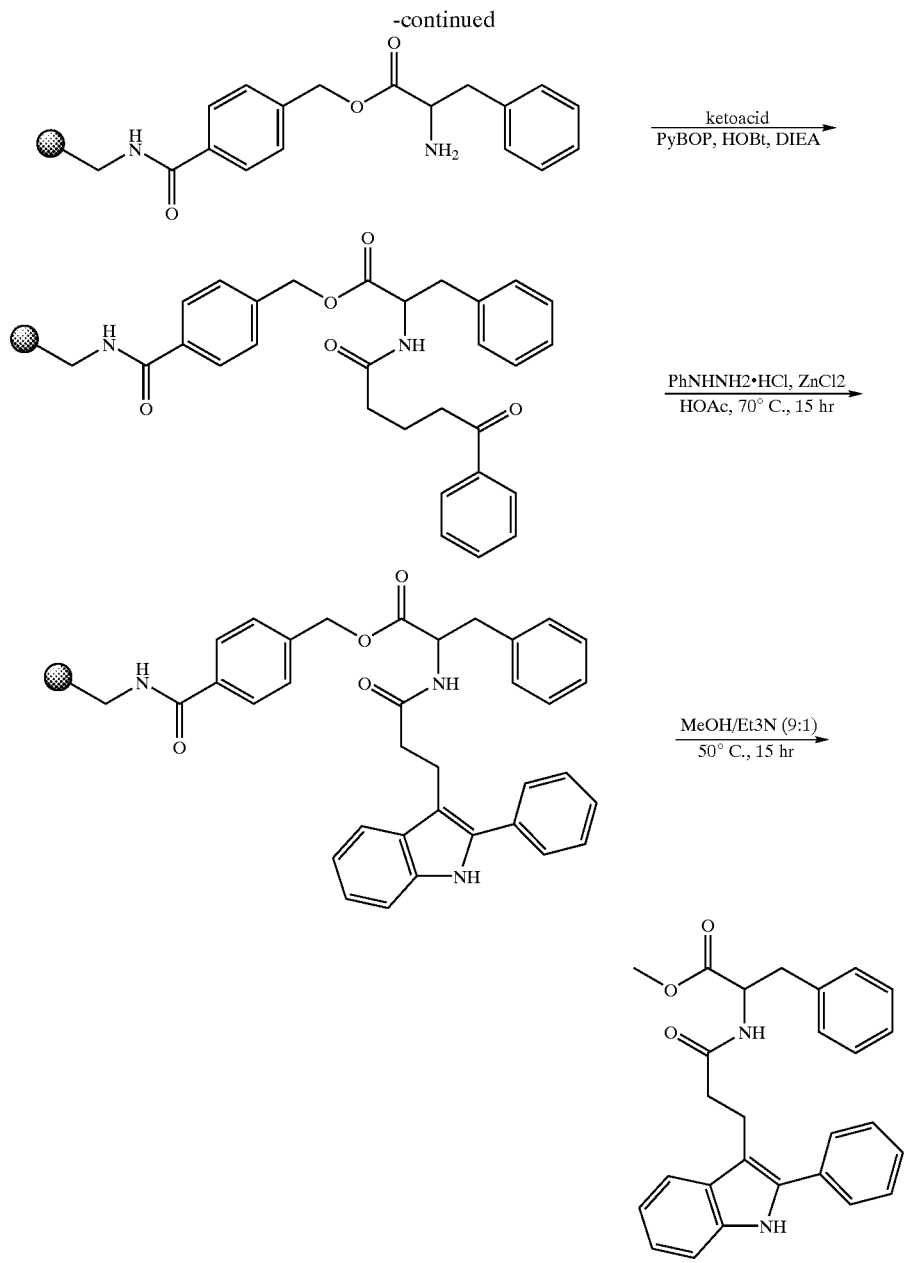

Samples 1A, 1AA, 1B and 1BB in Table 1 are controls that illustrate that the metal ions (Ag and Ni) are rapidly washed out of non-functionalized crosslinked polystyrene beads. The amount of metal salt (Ag and Ni nitrate) remaining on the resin is shown for polystyrene crosslinked with divinylbenzene after several different treatments. The amount of salt remaining on the resin is shown in Table 1 after the metal tag is added and the resin with the tag has been rinsed ("wash-1"), then again after the resin has either been treated with $Na_2S$ and rinsed a second time or rinsed a second time without $Na_2S$ treatment ("wash-2"). The conditions for tagging the support, for applying the $Na_2S$, and for the wash steps are shown in the footnotes to Table 1.

The data for Samples 1C, 1CC, 1D and 1DD illustrate that the amine functional group increases the affinity of the resin to absorb and retain the labeling metal, in sharp contrast to the non-functionalized polystyrene-divinylbenzene resin (Samples 1A, 1AA, 1B and 1BB), which has little or no affinity for metals. In these examples, the amount of salt remaining on the resin is shown in Table 1 after the metal tag is added and the resin with the tag has been rinsed ("wash-1"), then again after the resin has either been treated with $Na_2S$ and rinsed a second time or rinsed a second time without $Na_2S$ treatment ("wash-2"). For the samples that were treated with $Na_2S$, an HMBA linker was then coupled to the amine group of the resin, followed by the Fischer indole synthesis. The metal content of the support is shown after each of these steps.

It can be seen that treatment of the resins with $Na_2S$ enhances the resin's ability to retain the metal. This is believed to be the result of conversion of the soluble metal salts (e.g.nitrates) into insoluble metal sulfides. The $Na_2S$ treatment is therefore a critical component for a successful encoding process, as the untreated resins lose metal content during subsequent steps (see next example). It can also be seen in this example that retention of silver ion is much better than retention of nickel ion.

In Examples 1E, 1EE, 1F and 1FF, the same steps are carried out starting with an alcohol terminated polystyrene support unit that has an HMBA linker attached to it. The metal tags are attached to the HMBA functionalized beads, and the $Na_2S$ treatment is then carried out on the metal tagged beads. As in the earlier examples, some of the metal tagged HMBA functionalized beads are not treated with $Na_2S$ so that the $Na_2S$ treated beads can be compared with those that have not been treated with $Na_2S$. In these examples, the HMBA functionalized beads have a better affinity for the metal tags than polystyrene, but not as good an affinity as the beads that were made by attaching the HMBA linker to amine functionalized polystyrene. Comparison with the data shown in Samples 1A, 1AA, 1B and 1BB shows that the tagging metal does not adhere to polystyrene unless there is some kind of funtionality bound to the polystyrene, regardless of whether the polystyrene is treated with $Na_2S$. As in the earlier examples, the metal tags are retained more successfully after $Na_2S$ treatment, and Ag is retained better than Ni after the $Na_2S$ treatment.

Finally, the 3-substituted 2-arylindole products that were made by the Fischer indole synthesis had the same purity (>90% by HPLC and NMR) and yield whether or not a metal ion marker was used. Therefore, the presence of the metal does not appear to interfere with the chemical reactions of the supported organic compounds.

then one of the 4 Y-compounds is joined, and finally $Z_1$ is attached, followed by cyclization to yield an indole. The couplings of the compounds and linking groups to the beads are all carried out using standard methods.

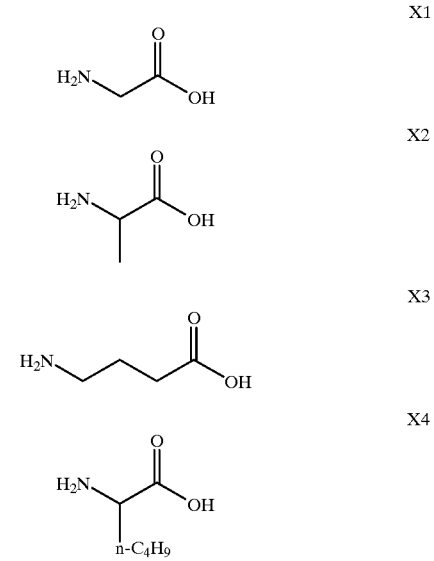

TABLE 1

Metal content (ppm) in the resins at various stages of solid phase synthesis

| Sample | Resin | Tagging | wash-1 | $Na_2S$ | wash-2 | linker | Phe | ketoacid | indole | cleave |
|---|---|---|---|---|---|---|---|---|---|---|
| 1A | PS-DVB | Ag | 111 | yes | 40 | | | | | |
| 1AA | PS-DVB | Ag | 111 | no | 29 | | | | | |
| 1B | PS-DVB | Ni | <70 | yes | <20 | | | | | |
| 1BB | PS-DVB | Ni | <70 | no | <30 | | | | | |
| 1C | PS-CH2NH2 | Ag | 47,200 | yes | 49,800 | 30,100 | 27,100 | 23,000 | 20,700 | 25,000 |
| 1CC | PS-CH2NH2 | Ag | 47,200 | no | 10,200 | | | | | |
| 1D | PS-CH2NH2 | Ni | 5,900 | yes | 1,900 | 1,520 | 210 | 63 | | 16 |
| 1DD | PS-CH2NH2 | Ni | 5,900 | no | 1,400 | | | | | |
| 1E | PS-HMBA | Ag | 2,300 | yes | 4,800 | | 4,700 | 4,200 | 10,600 | 4,900 |
| 1EE | PS-HMBA | Ag | 2,300 | no | 91 | | | | | |
| 1F | PS-HMBA | Ni | 3,500 | yes | 800 | | 152 | <50 | <50 | <20 |
| 1FF | PS-HMBA | Ni | 3,500 | no | 200 | | | | | |

Tagging: $AgNO_3$: 0.25M in 1:1 EtOH:$CH_3CN$ for 30 min; $Ni(NO_3)_2$: ~0.1M in EtOH:$CH_3CN$ for 30 min.
Wash-1: EtOH 3X; THF-DCM 3X;
Na2S treatment: 0.1M solution in DMF:EtOH:H2 (6:1:1) for 30 min;
Wash-2: DMF 3X; DMSO 3X; CH3CN: 1N HCl (2:1) 3X; DMF 3X; THF-DCM 3X;

Example 2

This example demonstrates the effect of pre-sulfurization of the resin in enhancing the absorption of metal ions. It also demonstrates the use of an encoding scheme which in this case yields a binary encoded library.

A set of four libraries with the same building blocks were synthesized so that the effect of $Na_2S$ treatment in the encoding process can be observed, and so that the effect of including a sulfur-containing group (3 methylated cystein units) with HMBA as the linker group can be determined. The combined effect of having both a sulfur-containing group in the linker and the $Na_2S$ treatment can also be observed.

The libraries are all of the same dimensions: 7×4×1, with the building blocks shown below. One of the 7 X-compounds is attached first to the resin or linker group, -continued

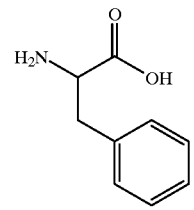

-continued

X6
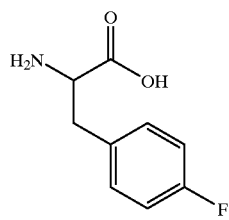

X7
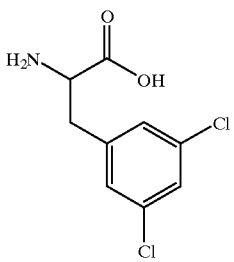

Y1
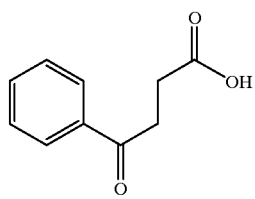

Y2
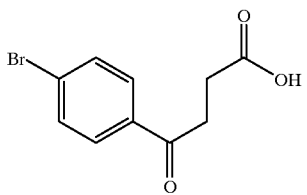

Y3
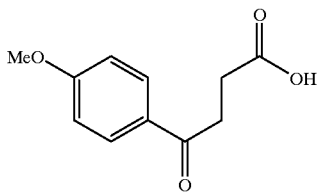

Y4
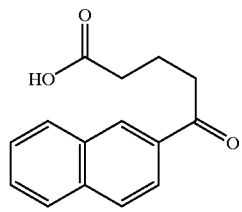

Z1
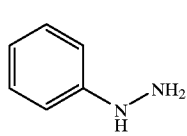

Four libraries are constructed to provide a comparison of the effects of the $Na_2S$ treatments, the effects of using a sulfur-containing group as part of the linker (i.e. between the HMBA and the polystyrene resin), and the combined effects of both $Na_2S$ treatment and the sulfur-containing group in the linker, as follows:

2A: PS-HMBA (no sulfur-containing group before HMBA in the linker), no $Na_2S$ treatment after the X and Y encoding steps;

2B: PS-HMBA (no sulfur-containing group before HMBA in the linker), $Na_2S$ treatment after both encoding steps;

2C: PS-(Cys')$_3$-HMBA, $Na_2S$ treatment after the X encoding step, but no $Na_2S$ treatment during the Y encoding step;

2D: PS-(Cys')$_3$-HMBA, $Na_2S$ treatment after both encoding steps.

The encoding tables and conditions are:

| X dimension encoding table | | | |
|---|---|---|---|
| Subunit | $Pd^{106}$ | Rh | $Pd^{108}$ |
| X1 | 0 | 0 | 1 |
| X2 | 0 | 1 | 0 |
| X3 | 0 | 1 | 1 |
| X4 | 1 | 0 | 0 |
| X5 | 1 | 0 | 1 |
| X6 | 1 | 1 | 0 |
| X7 | 1 | 1 | 1 |
| Tag concentration | 0.001 M | 0.005 M | 0.001 M |

| Y dimension encoding table | | |
|---|---|---|
| Subunit | Co | Ru |
| Y1 | 0 | 0 |
| Y2 | 0 | 1 |
| Y3 | 1 | 0 |
| Y4 | 1 | 1 |
| Tag concentration | 0.1 M | 0.008 M |

The metals were all added as soluble nitrate salts. The resin beads, after each of the first two building block couplings, were treated with the tag solution mixtures (DMF:$H_2O$ 9:1) for one hour, and then were washed with DMF:$H_2O$ (9:1) 3 times. After the tagging steps, some of the beads were treated with a solution of $Na_2S$, 0.1M in DMF:$H_2O$ (4:1) for one hour. The beads that were treated with $Na_2S$ and those that were not treated with $Na_2S$ were all rinsed with DMF:$H_2O$ (9:1) 3 times; then rinsed alternately with DMF and DMF: 1N HCl (9:1) 3 times; then DMF 3 times; and finally THF-DCM 3 times.

After the Y dimension encoding, the resins for each library were pooled together and then subjected to the Fisher-Indole cyclization reaction, under the following conditions: 0.5 M PhNHNH$_2$.HCl-ZnCl$_2$/HOAc at 70° C. overnight. The resins were washed and dried.

A portion of the resin from each library ((2A–2D) was cleaved to give a mixture of the 2-arylindoles. The yield and purity of the products were checked. The resin beads were then digested in nitric acid and analyzed in an ICP-MS instrument for bulk metal content. The results are shown in the following table:

| Library | Resin (mg) | Product (mg) | Metal content (ppm) analyzed by ICP-MS | | | | | |
|---|---|---|---|---|---|---|---|---|
| | | | Pd106 | Rh | Pd108 | Co | Ru | Zn |
| 2A | 55 | 13.5 mg | 11 | 54 | 9 | 1 | 5 | 93 |
| 2B | 44.3 | 9.7 mg | 176 | 178 | 347 | 171 | 412 | 686 |
| 2C | 49.9 | 7.7 mg | 361 | 514 | 518 | <1 | 249 | 5832 |
| 2D | 49.2 | 7.7 mg | 503 | 383 | 473 | 526 | 600 | 4860 |

It is clear that the resin beads in library 2A do not have enough of the encoding metal left at the end of synthesis to provide an identification of the metal code. In the similar library 2B, which-was treated with $Na_2S$ in both encoding steps, a significant amount of metal tag remained after cleavage of the ligand. For the resins that have the methyl-cystein tripeptide included in the linker, the metal content was high, except for 2C where the Y dimension encoding was done without $Na_2S$ treatment, and the Co was therefore low.

Single bead analyses are shown in the tables for Libraries 1B, 1C, and 1D for the experiments where the beads were also treated with $Na_2S$.

A number of beads from each library were cleaved (5 μl of 10%TEA/MeOH at 50° C. for 15 hr) individually to give one compound per bead. The excess reagent was removed by vacuum, and the compound extracted with 5 μl of DMSO. The compound solution in DMSO was then diluted to 25 μl with 2:1 $H_2O:CH_3CN$ and analyzed by LC-MS to identify the structure. The resin bead was then subjected to ETV-ICP-MS (electrothermal vaporization-ICP-MS) for metal content analysis. Upon examination of the relative intensity of each metal within a library, a threshhold level was chosen such that levels above the threshhold indicate the presence of the encoding metal, and levels below the threshhold indicate the absence of the encoding metal. A binary digit 1 represents the presence, and 0 represents the absence of the encoding metal. In case of encoding failure, no threshhold level can be set. The results for each library are shown in the following tables:

Library 2B (PS-HMBA Resin, with $Na_2S$ treatment)

| Bead # | Relative Intensity (ppm) | | | | | | Binary Code | | | | | | Subunit By LC-MS | | | |
|---|---|---|---|---|---|---|---|---|---|---|---|---|---|---|---|---|
| | $Pd^{106}$ | Rh | $Pd^{108}$ | Co | Ru | Zn | $Pd^{106}$ | Rh | $Pd^{108}$ | Co | Ru | X# | Y# | X# | Y# |
| 1 | 1005 | 17 | 896 | 182 | 242 | 271 | 1 | 0 | 1 | 1 | 1 | 5 | 4 | 7 | 4 |
| 2 | 793 | 10 | 771 | 1 | 42 | 811 | 1 | 0 | 1 | 0 | 1 | 5 | 2 | 7 | 2 |
| 3 | 1001 | 14 | 46 | 135 | 7 | 1214 | 1 | 0 | 0 | 1 | 0 | 4 | 3 | 6 | 3 |
| 4 | 8 | 12 | 11 | 82 | 3 | 1324 | 0 | 0 | 0 | 1 | 0 | — | 3 | 2 | 3 |
| 5 | 610 | 10 | 591 | 1 | 78 | 684 | 1 | 0 | 1 | 0 | 1 | 5 | 2 | 7 | 2 |
| 6 | 22 | 13 | 823 | 1 | 5 | 2163 | 0 | 0 | 1 | 0 | 0 | 1 | 1 | 1 | 1 |
| 7 | 410 | 8 | 384 | 1 | 67 | 580 | 1 | 0 | 1 | 0 | 1 | 5 | 2 | 7 | 2 |
| 8 | 388 | 13 | 19 | 195 | 117 | 255 | 1 | 0 | 0 | 1 | 1 | 4 | 4 | 4 | 4 |
| 9 | 814 | 11 | 822 | 231 | 143 | 223 | 1 | 0 | 1 | 1 | 1 | 5 | 4 | 7 | 4 |
| 10 | 468 | 7 | 475 | 1 | 48 | 764 | 1 | 0 | 1 | 0 | 1 | 5 | 2 | 5 | 2 |
| 11 | 960 | 15 | 47 | 74 | 8 | 818 | 1 | 0 | 0 | 1 | 0 | 4 | 3 | 6 | 3 |
| 12 | 1130 | 18 | 56 | 239 | 125 | 184 | 1 | 0 | 0 | 1 | 1 | 4 | 4 | 6 | 4 |
| 13 | 1000 | 16 | 947 | 181 | 143 | 270 | 1 | 0 | 1 | 1 | 1 | 5 | 4 | 7 | 4 |
| 14 | 24 | 15 | 791 | 123 | 12 | 9290 | 0 | 0 | 1 | 1 | 0 | 1 | 3 | 1 | 3 |
| 15 | 13 | 23 | 23 | 51 | 6 | 134 | 0 | 0 | 0 | 1 | 0 | — | 3 | 2 | 3 |
| 16 | 32 | 886 | 1567 | 153 | 102 | 438 | 0 | 1 | 1 | 1 | 1 | 3 | 4 | 3 | 4 |
| 17 | 1264 | 21 | 42 | 161 | 140 | 209 | 1 | 0 | 0 | 1 | 1 | 4 | 4 | 6 | 4 |
| 18 | 11 | 21 | 18 | 238 | 105 | 188 | 0 | 0 | 0 | 1 | 1 | — | 4 | 2 | 4 |
| 19 | 22 | 579 | 669 | 201 | 136 | 334 | 0 | 1 | 1 | 1 | 1 | 3 | 4 | 3 | 4 |
| 20 | 21 | 15 | 681 | 50 | 8 | 1732 | 0 | 0 | 1 | 1 | 0 | 1 | 3 | 1 | 3 |
| 21 | 16 | 11 | 395 | 83 | 4 | 1207 | 0 | 0 | 1 | 1 | 0 | 1 | 3 | 1 | 3 |
| 22 | 47 | 823 | 5607 | 3 | 118 | 983 | 0 | 1 | 1 | 0 | 1 | 3 | 2 | 3 | 2 |
| 23 | 678 | 22 | 683 | 64 | 7 | 935 | 1 | 0 | 1 | 1 | 0 | 5 | 3 | 5 | 3 |
| 24 | 51 | 485 | 8613 | 4 | 10 | 559 | 0 | 1 | 1 | 0 | 0 | 3 | 1 | 3 | 1 |
| 25 | 37 | 625 | 3274 | 2 | 116 | 1123 | 0 | 1 | 1 | 0 | 1 | 3 | 2 | 3 | 2 |
| 26 | 499 | 21 | 46 | 218 | 113 | 226 | 1 | 0 | 0 | 1 | 1 | 4 | 4 | 4 | 4 |
| 27 | 480 | 19 | 36 | 129 | 121 | 148 | 1 | 0 | 0 | 1 | 1 | 4 | 4 | 4 | 4 |
| 28 | 512 | 14 | 30 | 60 | 13 | 269 | 1 | 0 | 0 | 1 | 0 | 4 | 3 | 4 | 3 |
| 29 | 418 | 12 | 447 | 2 | 6 | 793 | 1 | 0 | 1 | 0 | 0 | 5 | 1 | 5 | 1 |
| 30 | 54 | 726 | 8007 | 173 | 11 | 1191 | 0 | 1 | 1 | 1 | 0 | 3 | 3 | 3 | 3 |
| 31 | 648 | 15 | 668 | 1 | 5 | 719 | 1 | 0 | 1 | 0 | 0 | 5 | 1 | 5 | 1 |
| 32 | 47 | 589 | 4394 | 96 | 8 | 2027 | 0 | 1 | 1 | 1 | 0 | 3 | 3 | 3 | 3 |
| 33 | 459 | 21 | 45 | 172 | 173 | 234 | 1 | 0 | 0 | 1 | 1 | 4 | 4 | 4 | 4 |
| 34 | 24 | 879 | 1859 | 2 | 11 | 1480 | 0 | 1 | 1 | 0 | 0 | 3 | 1 | 3 | 1 |
| 35 | 480 | 14 | 496 | 1 | 4 | 754 | 1 | 0 | 1 | 0 | 0 | 5 | 1 | 5 | 1 |
| 36 | 21 | 11 | 360 | 76 | 3 | 1230 | 0 | 0 | 1 | 1 | 0 | 1 | 3 | 1 | 3 |
| 37 | 20 | 560 | 1753 | 124 | 5 | 1887 | 0 | 1 | 1 | 1 | 0 | 3 | 3 | 3 | 3 |
| | 200 | 200 | 200 | 200 | 40 | | ←======Threshhold levels | | | | | | | | |

Metal codes for 2B are generally readable, except that the Rh data were not reliable. Loss of the Rh tag during reactions resulted in false negative readings of Rh content in several of the experiments. All mistakes in 2B are caused by the loss of Rh from the Rh coded beads. Higher Rh tagging concentrations would be needed for PS-HMBA resin to provide reliable data with a Rh tag.

Library 2C (PS-(Cys')₃-HMBA Resin, Y dimension encoding had no Na₂S treatment)

| | Relative Intensity (ppm) | | | | | | Binary Code | | | | | Subunit | | By LC-MS | |
|---|---|---|---|---|---|---|---|---|---|---|---|---|---|---|---|
| Bead # | Pd$^{106}$ | Rh | Pd$^{108}$ | Co | Ru | Zn | Pd$^{106}$ | Rh | Pd$^{108}$ | Co | Ru | X# | Y# | X# | Y# |
| 1 | 1949 | 25 | 1910 | 1 | 8 | 644 | 1 | 0 | 1 | | | 5 | | 5 | 1 |
| 2 | 72 | 1381 | 2479 | 1 | 12 | 3801 | 0 | 1 | 1 | | | 3 | | 0 | 0 |
| 3 | 61 | 50 | 1041 | 1 | 11 | 1516 | 0 | 0 | 1 | | | 1 | | 1 | 1 |
| 4 | 61 | 27 | 3174 | 0 | 86 | 1330 | 0 | 0 | 1 | | | 1 | | 1 | 2 |
| 5 | 28 | 557 | 1217 | 0 | 4 | 4834 | 0 | 1 | 1 | | | 3 | | 0 | 0 |
| 6 | 2094 | 293 | 88 | 0 | 94 | 427 | 1 | 1 | 0 | | | 6 | | 6 | 4 |
| 7 | 114 | 1974 | 3000 | 0 | 9 | 5010 | 1 | 1 | 1 | | | 7 | | 0 | 0 |
| 8 | 22 | 189 | 48 | 0 | 46 | 614 | 0 | 1 | 0 | | | 2 | | 2 | 2 |
| 9 | 990 | 24 | 64 | 0 | 8 | 591 | 1 | 0 | 0 | | | 4 | | 4 | 3 |
| 10 | 110 | 2137 | 8658 | 0 | 111 | 1169 | 1 | 1 | 1 | | | 7 | | 2 | 2 |
| 11 | 48 | 45 | 1156 | 0 | 99 | 2604 | 0 | 0 | 1 | | | 1 | | 1 | 2 |
| 12 | 4466 | 28 | 4589 | 0 | 99 | 1057 | 1 | 0 | 1 | | | 5 | | 5 | 2 |
| 13 | 2453 | 261 | 81 | 0 | 85 | 544 | 1 | 1 | 0 | | | 6 | | 6 | 2 |
| 14 | 2168 | 89 | 79 | 0 | 4 | 2720 | 1 | 1 | 0 | | | 6 | | 0 | 0 |
| 15 | 2132 | 138 | 2042 | 0 | 82 | 961 | 1 | 1 | 1 | | | 7 | | 7 | 2 |
| 16 | 2372 | 30 | 2389 | 0 | 104 | 748 | 1 | 0 | 1 | | | 5 | | 5 | 2 |
| 17 | 1451 | 31 | 48 | 0 | 68 | 155 | 1 | 0 | 0 | | | 4 | | 4 | 2 |
| | 500 | 70 | 500 | | | | ←===== threshhold levels | | | | | | | | |

Library 2C illustrates the critical effect of Na₂S treatment after the tagging step. In the X dimension encoding process, the tag metals were converted to less soluble metal sulfides. All X dimension codes are readable, though there are errors which can be corrected by adjustment of the threshold levels for presence of the metal. In Y dimension encoding, the Na₂S treatment step was skipped, and the Y dimension codes are unreadable. For Co, the lack of Na₂S resulted in the loosely bound Co being completely washed out of the beads. For Ru, the problem is the migration of tag metal from coded beads to uncoded beads.

Library 2D (PS-(Cys')₃-HMBA Resin, Na₂S treatment in all encoding steps)

| Sample | Relative Intensity | | | | | | Binary Code | | | | | Decoded LC-MS | | | |
|---|---|---|---|---|---|---|---|---|---|---|---|---|---|---|---|
| Bead # | Pd$^{106}$ | Rh | Pd$^{108}$ | Co | Ru | Zn | Pd$^{106}$ | Rh | Pd$^{108}$ | Co | Ru | X# | Y# | X# | Y# |
| 1 | 45 | 19 | 1356 | 678 | 163 | 804 | 0 | 0 | 1 | 1 | 1 | 1 | 4 | 1 | 4 |
| 2 | 2116 | 146 | 2249 | 766 | 5 | 1841 | 1 | 1 | 1 | 1 | 0 | 7 | 3 | 7 | 3 |
| 3 | 1289 | 17 | 41 | 1 | 2 | 661 | 1 | 0 | 0 | 0 | 0 | 4 | 1 | 4 | 1 |
| 4 | 3981 | 19 | 83 | 1 | 2 | 365 | 1 | 0 | 0 | 0 | 0 | 4 | 1 | 4 | 1 |
| 5 | 1719 | 110 | 1687 | 1156 | 264 | 1330 | 1 | 1 | 1 | 1 | 1 | 7 | 4 | 7 | 4 |
| 6 | 2799 | 57 | 3053 | 1 | 3 | 1265 | 1 | 0 | 1 | 0 | 0 | 5 | 1 | 7 | 1 |
| 7 | 1123 | 17 | 44 | 327 | 2 | 1640 | 1 | 0 | 0 | 1 | 0 | 4 | 3 | 4 | 3 |
| 8 | 2155 | 21 | 54 | 1 | 2 | 349 | 1 | 0 | 0 | 0 | 0 | 4 | 1 | 4 | 1 |
| 9 | 1120 | 13 | 40 | 1 | 2 | 473 | 1 | 0 | 0 | 0 | 0 | 4 | 1 | 4 | 1 |
| 10 | 1042 | 20 | 46 | 307 | 2 | 1420 | 1 | 0 | 0 | 1 | 0 | 4 | 3 | 4 | 3 |
| 11 | 2554 | 34 | 3147 | 1 | 3 | 448 | 1 | 0 | 1 | 0 | 0 | 5 | 1 | 5 | 1 |
| 12 | 2087 | 27 | 2210 | 1 | 3 | 924 | 1 | 0 | 1 | 0 | 0 | 5 | 1 | 5 | 1 |
| 13 | 47 | 11 | 2073 | 404 | 21 | 695 | 0 | 0 | 1 | 1 | 1 | 1 | 4 | 1 | 4 |
| 14 | 40 | 201 | 47 | 386 | 2 | 620 | 0 | 1 | 0 | 1 | 0 | 2 | 3 | 2 | 3 |
| 15 | 1851 | 25 | 50 | 2 | 2 | 260 | 1 | 0 | 0 | 0 | 0 | 4 | 1 | 4 | 1 |
| 16 | 62 | 21 | 1267 | 2 | 97 | 464 | 0 | 0 | 1 | 0 | 1 | 1 | 2 | 1 | 2 |
| 17 | 70 | 45 | 2109 | 1 | 8 | 1324 | 0 | 0 | 1 | 0 | 0 | 1 | 1 | 1 | 1 |
| 18 | 45 | 19 | 1614 | 1 | 2 | 1757 | 0 | 0 | 1 | 0 | 0 | 1 | 1 | 1 | 1 |
| 19 | 4000 | 29 | 4000 | 1 | 3 | 430 | 1 | 0 | 1 | 0 | 0 | 5 | 1 | 5 | 1 |
| 20 | 76 | 294 | 79 | 770 | 95 | 760 | 0 | 1 | 0 | 1 | 1 | 2 | 4 | 2 | 4 |
| 21 | 58 | 22 | 1462 | 429 | 130 | 262 | 0 | 0 | 1 | 1 | 1 | 1 | 4 | 1 | 4 |
| 22 | 53 | 18 | 3422 | 4 | 165 | 385 | 0 | 0 | 1 | 0 | 1 | 1 | 2 | 1 | 2 |
| 23 | 69 | 24 | 4119 | 474 | 8 | 548 | 0 | 0 | 1 | 1 | 0 | 1 | 3 | 1 | 3 |
| 24 | 37 | 23 | 994 | 2 | 5 | 289 | 0 | 0 | 1 | 0 | 0 | 1 | 1 | 1 | 1 |
| 25 | 1560 | 19 | 59 | 364 | 157 | 450 | 1 | 0 | 0 | 1 | 1 | 4 | 4 | 4 | 4 |
| 26 | 32 | 14 | 1206 | 1 | 4 | 1052 | 0 | 0 | 1 | 0 | 0 | 1 | 1 | 1 | 1 |
| 27 | 1083 | 15 | 37 | 1 | 3 | 726 | 1 | 0 | 0 | 0 | 0 | 4 | 1 | 4 | 1 |
| 28 | 106 | 936 | 2619 | 2 | 4 | 1206 | 0 | 1 | 1 | 0 | 0 | 3 | 1 | 3 | 1 |
| 29 | 2059 | 27 | 61 | 1 | 3 | 319 | 1 | 0 | 0 | 0 | 0 | 4 | 1 | 4 | 1 |
| 30 | 101 | 25 | 2337 | 2 | 113 | 556 | 0 | 0 | 1 | 0 | 1 | 1 | 2 | 1 | 2 |
| 31 | 67 | 26 | 1771 | 2 | 186 | 452 | 0 | 0 | 1 | 0 | 1 | 1 | 2 | 1 | 2 |
| 32 | 63 | 28 | 2000 | 1 | 7 | 390 | 0 | 0 | 1 | 0 | 0 | 1 | 1 | 1 | 1 |

-continued

Library 2D (PS-(Cys')₃-HMBA Resin, Na₂S treatment in all encoding steps)

| Sample Bead # | Relative Intensity | | | | | | Binary Code | | | | | Decoded | | LC-MS | |
|---|---|---|---|---|---|---|---|---|---|---|---|---|---|---|---|
| | $Pd^{106}$ | Rh | $Pd^{108}$ | Co | Ru | Zn | $Pd^{106}$ | Rh | $Pd^{108}$ | Co | Ru | X# | Y# | X# | Y# |
| 33 | 61 | 16 | 1748 | 1 | 3 | 398 | 0 | 0 | 1 | 0 | 0 | 1 | 1 | 1 | 1 |
| 34 | 47 | 299 | 55 | 811 | 118 | 454 | 0 | 1 | 0 | 1 | 1 | 2 | 4 | 2 | 4 |
| 35 | 51 | 450 | 63 | 733 | 214 | 665 | 0 | 1 | 0 | 1 | 1 | 2 | 4 | 2 | 4 |
| 36 | 71 | 24 | 1677 | 672 | 167 | 281 | 0 | 0 | 1 | 1 | 1 | 1 | 4 | 1 | 4 |
| 37 | 1763 | 19 | 53 | 5 | 110 | 273 | 1 | 0 | 0 | 0 | 1 | 4 | 2 | 4 | 2 |
| | 1000 | 100 | 1000 | 100 | 20 | | ←======== threshhold levels | | | | | | | | |

Library 2D has been successfully encoded. Among the beads cleaved and analyzed, all decoded structures matched the LC-MS structure, except for bead no. 6, which would have been correct if the threshold for Rh had been set slightly lower (e.g. relative intensity=50).

What is claimed is:

1. A method of preparing an encoded combinatorial library comprising a plurality of ligand-bearing support units, wherein said ligand-bearing support units comprise (a) a solid carrier, (b) one or more ligands covalently bound to said solid carrier, and (c) a plurality of encoding metal salts impregnated on said support unit, said metal salts providing a code for identifying said ligand, comprising the steps of:

(1) providing support units comprising a solid carrier having functional groups, said functional groups being optionally connected to linker groups, said linker groups being organic residues covalently bound to the functional groups of said solid carrier and having functional groups for covalent binding to said ligand;

(2) covalently attaching a ligand or a first sub-unit of a ligand that will have more than one sub-unit to the functional group of said carrier or to the functional group of an optional linker group, said sub-unit having a functional group for covalent binding to a second sub-unit;

(3) impregnating said support unit with one or more encoding metal salts, said salts being comprised of one or more encoding metal cations, said encoding metal cations being distributed in their natural isotope abundance or in a non-natural isotope abundance, wherein the encoding metal cations provide a code for identifying the ligand or sub-unit that is attached to said support unit, wherein the encoding metal salts are impregnated onto the support unit by treating the support unit with a solution of a soluble salt of the encoding metal cations to form a support unit comprising the soluble encoding metal cations, and then treating said support unit comprising said soluble encoding metal salts with a solution of a salt having an anion that forms insoluble or poorly soluble salts when combined with said encoding metal salts, thereby yielding a stabilized encoding metal salt, said salt being stabilized against dissolution from said support unit;

wherein step (3) is optionally carried out before or after step (2) or concurrently with step (2).

2. A method of preparing an encoded combinatorial library comprising a plurality of ligand-bearing support units, as recited in claim 1, wherein said ligands comprise two or more sub-units, comprising the further steps of:

(1) covalently attaching a second sub-unit to the functional group of said first sub-unit, wherein said second sub-unit is optionally the same as the first sub-unit or different, wherein said second sub-unit optionally has a functional group that optionally may be used for adding a third sub-unit;

(2) impregnating said support unit with one or more encoding metal salts, said salts being comprised of one or more encoding metal cations, said encoding metal cations being distributed in their natural isotope abundance or in a non-natural isotope abundance, wherein said encoding metal cations provide a code for identifying said second sub-unit, wherein the encoding metal salts are impregnated onto the support unit by treating the support unit with a solution of a soluble salt of the encoding metal cation to form a support unit comprising a soluble encoding metal salt, and then treating said support unit comprising said soluble encoding metal salt with a solution of a salt having an anion that forms insoluble or poorly soluble salts when combined with said encoding metal cations, thereby yielding a stabilized encoding metal salt, said salt being stabilized against dissolution from said support unit; and (3) optionally repeating said steps (1) and (2) one or more times to add additional sub-units to form a ligand comprising a plurality of sub-units, said ligand being identifiable by measurement of the distribution of metal cations on said support unit;

wherein step (1) is optionally carried out before or after step (2) or concurrently with step (2) in each repetition of steps (1) and (2).

3. A method of preparing an encoded combinatorial library comprising a plurality of ligand-bearing support units, wherein said ligand-bearing support units comprise (a) a solid carrier, (b) one or more ligands covalently bound to said solid carrier, wherein said ligands are comprised of two or more sub-units, and (c) a plurality of encoding metal salts impregnated on said support unit, said metal salts providing a code for identifying said ligand, comprising the steps of:

(1) providing support units comprising a solid carrier having functional groups, said functional groups being optionally connected to linker groups, said linker groups being organic residues covalently bound to the functional groups of said solid carrier and having functional groups for covalent bonding to said ligand;

(2) covalently attaching a first sub-unit to the functional group of said carrier or to the functional group of said optional linker group, said sub-unit having a functional group for covalent bonding to a second sub-unit;

(3) impregnating said support unit with one or more encoding metal salts, said salts being comprised of one or more encoding metal cations, said encoding metal cations being distributed in their natural isotope abundance or in a non-natural isotope abundance, wherein the combination of encoding metal cations provides a code for identifying the sub-unit that is attached to said support unit, wherein the encoding metal salts are impregnated onto the support unit by treating the support unit with a solution of a soluble salt of the encoding metal cation to form a support unit comprising the soluble encoding metal salt, and then treating said support unit comprising said soluble encoding metal salt with a solution of a salt having an anion that forms insoluble or poorly soluble salts when combined with said encoding metal cations, thereby yielding an encoding metal salt that is stabilized against dissolution from said support unit;

(4) covalently attaching a second sub-unit to the functional group of said first sub-unit, wherein said second sub-unit may be the same as the first sub-unit or different, wherein said second sub-unit optionally has a functional group that optionally may be used for adding a third sub-unit;

(5) impregnating said support unit with one or more encoding metal salts, said salts being comprised of one or more encoding metal cations, said encoding metal cations being distributed in their natural isotope abundance or in a non-natural isotope abundance, wherein said encoding metal cations provide a code for identifying said second sub-unit, wherein the encoding metal salts are impregnated onto the support unit by treating the support unit with a solution of a soluble salt of the encoding metal cation to form a support unit comprising a soluble encoding metal salt, and then treating said support unit comprising said soluble encoding metal salt with a solution of a salt having an anion that forms insoluble or poorly soluble salts when combined with said encoding metal cations, thereby yielding an encoding metal salt that is stabilized against dissolution from said support unit;

(6) repeating said steps (4) and (5) one or more times to add additional sub-units to form a ligand comprising a plurality of sub-units, said ligand being identifiable by measurement of the distribution of metal cations on said support unit;

wherein step (2) is optionally carried out before or after step (3) or concurrently with step (3), step (4) is optionally carried out before or after step (5) or concurrently with step (5), and in subsequent repetitions of steps (4) and (5) as recited in step (6), step (4) is optionally carried out before or after step (5) or concurrently with step (5).

4. The method as recited in claim 3, wherein said solid carrier is a synthetic polymeric compound, and said support units are porous beads.

5. The method as recited in claim 4, wherein said polymeric compound is polystyrene, optionally crosslinked with divinylbenzene, wherein said polystyrene comprises functional groups, and said ligands or said optional linker groups are covalently bound to said functional groups of said polystyrene.

6. The method as recited in claim 3, wherein said encoding metal cations are selected from the group consisting of the transition metals, the lanthanides, the actinides, Sr, Ba, Tl, In, Sb, and Bi.

7. The method as recited in claim 5, wherein said encoding metal cations are selected from the group consisting of the Group VIIIB, IB and IIB transition metals.

8. The method as recited in claim 3, wherein said encoding metal cations are selected from the group consisting of Pd, Ru, Rh, Pt, Ag, Ni, Cu, Co, Hg, and individual isotopes thereof.

9. The method as recited in claim 3, wherein said anion is sulfide.

10. The method as recited in claim 1, wherein said library is made by a split-pool synthesis.

11. In a method of preparing a combinatorial library comprising a plurality of support units, wherein each support unit comprises (a) a solid carrier, (b) one or more ligands covalently bound to said solid carrier or to a linker group that is covalently bound to said solid carrier, and (c) one or more encoding metal salts impregnated on said support unit, wherein said encoding metal salts comprise encoding metal cations, the distribution of said cations providing a code that identifies said ligand or ligands, the improvement that said encoding metal cations are stabilized against dissolution by treatment of said support units with a solution that comprises one or more anions that form insoluble or poorly soluble salts of said encoding metal cations in the solvent or solvents which are used to prepare said combinatorial library, thereby yielding an encoding metal salt that is stabilized against dissolution.

12. The improvement as recited in claim 11, wherein said encoding metal cations form soluble salts with one or more anions selected from the group consisting of nitrates, hydroxides, chlorides, acetates, and sulfates, and said encoding metal cations form insoluble or poorly soluble salts with one or more anionic groups selected from the group consisting of sulfides, sulfates, oxides, hydroxides, halides and carbonates.

13. The improvement as recited in claim 11, wherein said encoding metal cations are selected from the group consisting of the transition metals, the lanthanides, the actinides, Sr, Ba, Tl, In, Sb, and Bi.

14. The improvement as recited in claim 11, wherein said anions are sulfide anions.

15. The improvement as recited in claim 11, wherein said encoding metal cations are selected from the group consisting of the Group VIIIB, IB and IIB transition metals.

16. The improvement as recited in claim 11, wherein said encoding metal cations are selected from the group consisting of Pd, Ru, Rh, Pt, Ag, Ni, Cu, Co, Hg, and individual isotopes thereof.

17. The method as recited in claim 4, wherein said polymeric compound is aminomethyl functionalized polystyrene.

18. The method as recited in claim 17, wherein said optional linker group is HMBA.

19. The method as recited in claim 11, wherein said solid carrier is aminomethyl functionalized polystyrene.

20. The method as recited in claim 19, wherein said linker group is HMBA.

* * * * *